United States Patent
Benesch et al.

(10) Patent No.: US 6,724,475 B2
(45) Date of Patent: Apr. 20, 2004

(54) APPARATUS FOR RAPIDLY MEASURING ANGLE-DEPENDENT DIFFRACTION EFFECTS ON FINELY PATTERNED SURFACES

(75) Inventors: Norbert Benesch, Nürnberg (DE); Claus Schneider, Bubenreuth (DE); Lothar Pfitzner, Erlangen (DE)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 09/968,587

(22) Filed: Oct. 1, 2001

(65) Prior Publication Data

US 2002/0101585 A1 Aug. 1, 2002

Related U.S. Application Data

(63) Continuation of application No. PCT/EP00/02894, filed on Mar. 31, 2000.

(30) Foreign Application Priority Data

Mar. 31, 1999 (DE) .......................................... 199 14 696

(51) Int. Cl.⁷ .............................................. G01N 21/00
(52) U.S. Cl. ................................................... 356/237.4
(58) Field of Search .......................... 356/237.1–237.6, 356/239.2–239.8, 300–334, 128–137

(56) References Cited

U.S. PATENT DOCUMENTS

| 4,655,592 A | 4/1987 | Allemand |
| 5,048,970 A | 9/1991 | Milosevic et al. |
| 5,414,747 A | 5/1995 | Ruud et al. |
| 5,637,873 A | 6/1997 | Davis et al. |
| 5,920,662 A | 7/1999 | Hinkov |

FOREIGN PATENT DOCUMENTS

| DE | 36 26 724 A1 | 2/1988 |
| DE | 198 24 624 A 1 | 2/1999 |
| EP | 1 035 408 A1 | 9/2000 |
| WO | WO 99/14575 | 3/1999 |

OTHER PUBLICATIONS

Michael R. Murnane et al.: "Developed Photoresist Metrology using Scatterometry", XP–000892239, SPIE vol. 2196, Mar. 1994, pp. 47–59.
International Search Report for PCT/EP00/02894, issued by the European Patent Office on Oct. 17, 2000.

Primary Examiner—Tu T. Nguyen
(74) Attorney, Agent, or Firm—Laurence A. Greenberg; Werner H. Stemer; Gregory L. Mayback (57) ABSTRACT

An apparatus for measuring angle-dependent diffraction effects includes a coherent radiation source, a device for deflecting the coherent radiation in different directions, a spherical or aspherical mirror or mirror segments configured to correspond to a spherical or aspherical mirror, and a detector unit for measuring the intensity of the radiation diffracted at a specimen. The radiation deflected in different directions is reflected by the mirror configuration in such a way that the coherent beam is deflected onto the specimen with different angles of incidence in a temporally successively sequential manner. For this purpose, the angle of incidence of the measuring beam is altered continuously or in small steps. The intensities of the direct reflection (zero-order diffraction) and also of the higher orders of diffraction that may occur are measured. This evaluation allows conclusions to be drawn regarding the form and material of the periodic structures examined.

28 Claims, 4 Drawing Sheets

APPARATUS FOR RAPIDLY MEASURING ANGLE-DEPENDENT DIFFRACTION EFFECTS ON FINELY PATTERNED SURFACES

CROSS-REFERENCE TO RELATED APPLICATION

This application is a continuation of copending International Application No. PCT/EP00/02894, filed Mar. 31, 2000, which designated the United States.

BACKGROUND OF THE INVENTION

FIELD OF THE INVENTION

The invention relates to an apparatus for rapidly measuring angle-dependent diffraction effects on finely patterned surfaces in the submicron range.

In semiconductor fabrication, line widths and profiles of patterned layers often have to be monitored during the fabrication process. Complying exactly with the specifications for the line width is of crucial importance for the functionality of a product. In addition, other structural parameters such as trench depth or sidewall inclination are also of major importance. Suitable measuring apparatuses are required for monitoring these fabrication parameters on lithography masks, semiconductor wafers, or other very finely patterned surfaces.

With the extremely small structural widths in the region of 0.25 $\mu$m that are used nowadays in semiconductor fabrication, conventional optical line width measuring apparatuses can no longer be used on account of diffraction and interference effects. Therefore, electron microscopes are used for measuring the profile of fine structures (<1 $\mu$m). On account of the stringent vacuum requirements, even very complex electron microscopes developed specifically for line width measurements have a comparatively low throughput. Consequently, after a fabrication step, only a small portion of the product wafers can be checked with regard to compliance with the process specifications. Furthermore, the long measuring times increase the probability of further batches being fabricated defectively until a process fault is detected. These dead times can cause major financial losses particularly in the case of the latest fabrication technologies with wafer diameters of 300 mm and very complex process steps. Moreover, only a small number of individual structures can be monitored on each wafer using electron microscopes, and so the measurements are not representative. Therefore, under certain circumstances, fabrication faults or the causes thereof will be identified only very belatedly. In order to check further structural parameters, so-called monitor wafers are additionally included (e.g. in deposition processes) in order to be able to determine layer thicknesses produced on unpatterned wafers or in order to enable the electron microscope to effect so-called cross section recordings, for which the semiconductor wafers must be destroyed. Primarily in the case of future large wafer diameters of 300 mm or more, these monitor wafers cause high costs, firstly on account of the pure material value and secondly because they significantly reduce the throughput of product wafers. In order to manage with the fewest possible monitor wafers and nevertheless to improve the product monitoring, what are required in semiconductor fabrication are cost-effective measurement methods for nondestructive and contamination-free checking of structural parameters on the product wafers. In this case, the measuring speed should be high enough that, e.g. after a critical process step, each product wafer can be monitored without significantly increasing the process time. Scattered light measurement offers one solution approach. In general, during this method, the measurement region to be examined is illuminated and the surface properties of the measurement region are inferred from the features of the reflected light. If there are periodic structures on the substrate and if coherent light is used, then diffraction and interference effects occur given a corresponding choice of wavelength. Said effects prevent a measurement in conventional optical apparatuses, but they are explicitly detected and evaluated in the case of scattered light measurement or diffraction analysis since they are characteristic of the structural parameters. In research, the so-called 2θ method has acquired a certain importance in recent years. In this case, the angle of incidence of the measuring beam is varied within the plane of incidence and the intensities of the orders of diffraction are measured as a function of the angle of incidence. With the aid of complex model calculations, it is possible to determine from this diffraction measurement various structural parameters such as line width, trench depth or edge inclination. However, the measurement configurations used hitherto for this purpose are not very flexible or are comparatively slow, structurally complex and expensive.

In previous realizations, the light source is moved by precise mechanical components or the specimen to be examined is itself rotated about the measurement point. This raises the costs of the apparatus and restricts the range of use of the method. Lens systems produce different angles of incidence, so that all that has to be moved is an optical element (e.g. mirror or prism), not the specimen. However, only limited angles of incidence can be realized even with complex lens configurations having a large aperture. Under certain circumstances, disturbing reflections occur at the interfaces.

Simultaneously producing a plurality of angles of incidence with the aid of a multiple beam splitter (e.g. reflection grating) in conjunction with an ellipsoidal mirror is proposed in German Published Patent Application DE 198 24 624. However, the angles of incidence are chosen when the measuring apparatus is constructed and so this choice is fixed and the number of angles of incidence that can be realized simultaneously is limited. Principally, however, the diffraction effects are simultaneously superimposed on the specimen structures for the different angles of incidence. Consequently, an angle-dependent measurement of diffraction intensities is not possible. By contrast, the apparatus in accordance with DE 198 24 624 enables the simultaneous measurement under different diffraction angles, which may be advantageous when comparing the measurement with a single simulated diffraction pattern.

A measurement method should be nondestructive, free of contamination, fast, simple, and robust. A promising approach for determining structural parameters is offered by so-called scattered light measurement: the angularly resolved intensity measurement of light that has been scattered at a substrate. Reflected or transmitted light is diffracted in the case of specimens having periodic structures. Regular semiconductor structures, e.g. in memory modules, can be imagined as a reflective amplitude or phase grating. If the grating vector is situated in the plane of incidence, then, for a given angle θi of incidence, the following grating equation holds true for the n-th order diffraction maximum with the angle $\theta_n$ of reflection $$\sin\theta_i + \sin\theta_n = n\frac{\lambda}{g}$$

In this case, λ describes the wavelength of the light used and g denotes the grating period. Accordingly, in addition to the direct reflection already present, higher-order diffraction maxima can arise if the wavelength of the light used is less than half the grating period. If the size of the structures examined lies in the region of the wavelength, then the simple scalar Fraunhofer diffraction equations can no longer be employed. Instead, a simulation of the intensity distribution requires the solution of the associated Maxwell's equations with the boundary conditions applicable to the respective grating. Efficient numerical methods, such as e.g. the so-called rigorous coupled wave analysis, have been developed for this purpose in previous years. The nonlinearities that occur allow generally valid statements only to a very limited extent, for which reason the concrete individual case must always be considered or numerically calculated for the assessment of diffraction effects on small structures. In this case, the intensities and also the phases of the orders of diffraction depend on the properties of the incident beam (angle, polarization, wavelength), on the examined grating structure (grating periods, line width, line height, layer structure, edge rounding, roughness) and on the material properties of the substrate (refractive index, absorption index).

A diffraction analysis according to the prior art can be broken down into a plurality of steps. First of all, the intensity of the scattered or diffracted light is measured. Afterward, the measured intensity distribution is compared with a simulated intensity distribution, the grating parameters being varied in a predetermined range. This simulation of the diffraction process is effected on the basis of a priori knowledge of the specimen. Those parameter values that lead to the best correspondence between measurement and simulation are accepted as practical approximations of the real grating parameters.

SUMMARY OF THE INVENTION

It is accordingly an object of the invention to provide an apparatus for rapidly measuring angle-dependent diffraction effects on finely patterned surfaces that overcomes the hereinafore-mentioned disadvantages of the heretofore-known devices of this general type and that utilizes a simplified measuring construction that reduces the apparatus costs, enables use as an integrated measuring apparatus, and considerably accelerates the measurement.

With the foregoing and other objects in view, there is provided, in accordance with the invention, an apparatus for measuring angle-dependent diffraction effects. The apparatus includes a coherent radiation source producing coherent radiation; a device for deflecting rays of the coherent radiation in different directions; a concentric mirror reflecting the rays arriving differently and sequentially one after the other from the device for deflecting the coherent radiation at a focal point; and a detector unit for measuring the intensity of the radiation diffracted by a specimen having a measuring point located at the focal point.

In accordance with a further feature of the invention, the concentric mirror includes mirror segments disposed to act as a single concentric mirror.

In accordance with a further feature of the invention, device for deflecting the coherent radiation includes an electrically regulated rotating mirror, a micro-optical module, or an electro-optical module.

In accordance with a further feature of the invention, the concentric mirror has an axis of symmetry; and the device for deflecting the coherent beam is situated on the axis of symmetry of the concentric mirror. Moreover, the concentric mirror can have a center point; and the measurement point on the specimen is disposed on the axis of symmetry of the concentric mirror symmetrically and equidistantly from the center point of the concentric mirror as the device for deflecting the coherent beam.

In accordance with a further feature of the invention, the concentric mirror has an axis of symmetry; the device for deflecting the coherent beam is situated on the axis of symmetry of the concentric mirror; and the rotating mirror has an axis of rotation coinciding with the axis of symmetry and is always impinged by the coherent beam at a point on the axis of symmetry.

In accordance with a further feature of the invention, the concentric mirror has a center point; and the measurement point on the specimen is disposed on the axis of symmetry of the concentric mirror symmetrically and equidistantly from the center point of the concentric mirror as the device for deflecting the coherent beam.

In accordance with a further feature of the invention, the detector unit includes a photodiode linear array, a plurality of individual diodes, a single large-area photodiode, photodiode arrays, or CCDs.

In accordance with a further feature of the invention, the apparatus includes a mirror reflecting the radiation diffracted at the specimen onto the detector. The mirror for directing the diffracted radiation indirectly onto the detector unit can resemble the concentric mirror. Together, the mirror and the concentric mirror can form a mirrored ring.

In accordance with a further feature of the invention, the electrically regulated rotating mirror is for further deflecting the diffracted radiation onto the detector element.

In accordance with a further feature of the invention, the apparatus including a radiation detector impinged upon by a beam when the deflection device is specifically positioned.

In accordance with a further feature of the invention, the apparatus includes a beam splitter splitting the beam to create partial beams, and a radiation detector being impinged upon by a partial beam from the beam splitter when the deflection device is specifically positioned.

In accordance with a further feature of the invention, the apparatus includes a position sensitive device detecting a change in the angle of incidence through tilting and surface undulations of the specimen; and a piezoelement correcting for the change in the angle of incidence through tilting and the surface undulations of the specimen when measured data is evaluated.

In accordance with a further feature of the invention, the apparatus includes a CCD detecting a change in the angle of incidence through tilting and surface undulations of the specimen; and a piezoelement correcting for the change in the angle of incidence through tilting and the surface undulations of the specimen when measured data is evaluated.

In accordance with a further feature of the invention, the apparatus includes an xy measurement table positioning the specimen to measure different measurement points on a specimen.

With the objects of the invention in view, there is also provided an assembly for measuring angle-dependent diffraction effects. The assembly includes an apparatus as described above. In addition, the assembly includes a positioner for positioning the apparatus relative to the specimen.

In accordance with a newly developed method of diffraction analysis, the required computation complexity can be decisively reduced if an exact quantitative evaluation is dispensed with and only a classification is performed instead. A quantity of specimens is measured and classified in classes by recording the diffraction pattern for each specimen and measuring the specimen by other methods. The classification of feature or quality classes is carried out primarily according to the results of the other methods. However, care should be taken to ensure that the diffraction patterns of specimens within a class are similar, i.e. the diffraction patterns of the specimens have features that can be identified as similar. A diffraction measurement can thus be effected before another e.g. destructive analysis, for instance electron microscopy, which then leads to the classification. The diffraction patterns are thus assigned to the feature or quality classes. The processes of classifying feature or quality classes and finding features in the diffraction patterns for assessment of similarity belong to the preparations for the actual diffraction measurement of unknown specimens.

An unknown specimen is then classified by measuring specimens and assigning the diffraction pattern to a class. Such specimens are classified in quality classes using the measurements by other methods. Specimens within a class have similar diffraction patterns. It is possible to assign an unknown specimen to a class using its diffraction pattern and conclude that it has similar physical properties to the remaining members of this class.

The advantages of this method are that a simulation from a priori data is no longer necessary, and that the measurement and evaluation can be effected nondestructively and very rapidly during a current fabrication process using a simple measuring configuration. This makes it possible to examine a large number of specimens in a short time.

Compared to German patent application No. DE 198 24 624, the present invention provides, for the first time, simultaneous production of a plurality of angles of incidence with the aid of a multiple beam splitter (e.g. reflection grating) in conjunction with an ellipsoidal mirror. However, the angles of incidence are chosen when the measuring apparatus is constructed, and so this choice is fixed and the number of angles of incidence that can be realized simultaneously is limited. Principally, however, the diffraction effects are superimposed simultaneously on the specimen structures for the different angles of incidence. Consequently, an angle-dependent measurement of diffraction intensities is not possible.

On account of the large number of influencing variables, the grating parameters can be unambiguously determined or classified only if there are a sufficient number of intensity measurement values available for the measurement point examined. For this purpose, it is possible to vary one or more parameters of the measuring beam (angle, polarization, wavelength) and to measure the intensities as a function of the variable quantities. Thus, the diffraction analysis still can be used for structural characterization even if, owing to small grating periods, only few if any orders of diffraction occur apart from the direct reflection (see grating equation).

A device for measuring angle-dependent diffraction effects includes a coherent radiation source, a device for deflecting the coherent radiation in different directions, a mirror configuration that directs the deflected radiation to a specimen location, and a detector unit for measuring the intensity of the radiation diffracted at a specimen. The radiation deflected in different directions is reflected by the mirror configuration in such a way that the coherent beam is deflected onto the specimen with different angles of incidence in a temporally successively sequential manner.

For this purpose, the angle of incidence of the measuring beam is altered continuously or in small steps. The intensities of the direct reflection (zero-order diffraction) and also of the higher orders of diffraction that may occur are measured. The evaluation of the intensity profiles as a function of the varied angle of incidence allows conclusions to be drawn regarding the form and material of the periodic structures examined.

In the present invention, for the first time, use is made of an electrically rotating and regulated mirror (so-called galvanometer scanner) in conjunction with a stationary, nonplanar mirror surface in order to vary the angle of incidence of the measuring beam for a 2θ diffraction analysis of a fixed measurement point. The measuring configuration makes it possible to move to large angular positions within milliseconds with an accuracy of a few $\mu$rad. As a result, it is possible to carry out a complete measurement with variation of the angle of incidence within a few tenths of a second. Furthermore, producing the different angles of incidence requires only a robust movable component (galvanometer scanner) and so the susceptibility to disturbance is reduced. The costs of the components used and also the space required for the measurement setup are comparatively small. Because the different angles of incidence are produced sequentially, exactly one incident measuring beam exists at each point in time. Consequently, superimposition of orders of diffraction does not occur. Irrespective of the type of structure examined, the intensities of all the diffraction maxima that can be detected by the detector can be measured and assigned. The approximately constant intensity of the measuring beam independently of the angle of incidence (in contrast to DE 198 24 624 A1) increases the measurement accuracy of the system. The same applies to the exclusive use of mirror surfaces instead of lenses with optical imaging errors.

Other features which are considered as characteristic for the invention are set forth in the appended claims.

Although the invention is illustrated and described herein as embodied in apparatus for rapidly measuring angle-dependent diffraction effects on finely patterned surfaces, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

In all the figures of the drawing, sub-features and integral parts that correspond to one another bear the same reference symbol in each case.

Measuring configurations are presented that can be used to vary the angle of incidence (perpendicular or azimuthal angle) of the measuring beam on a specific point of the specimen very rapidly, precisely and cost-effectively over a large range. Depending on the type of detector system used, only the direct reflection or, in addition, also higher orders of diffraction are measured for each angle of incidence.

Figure 1:
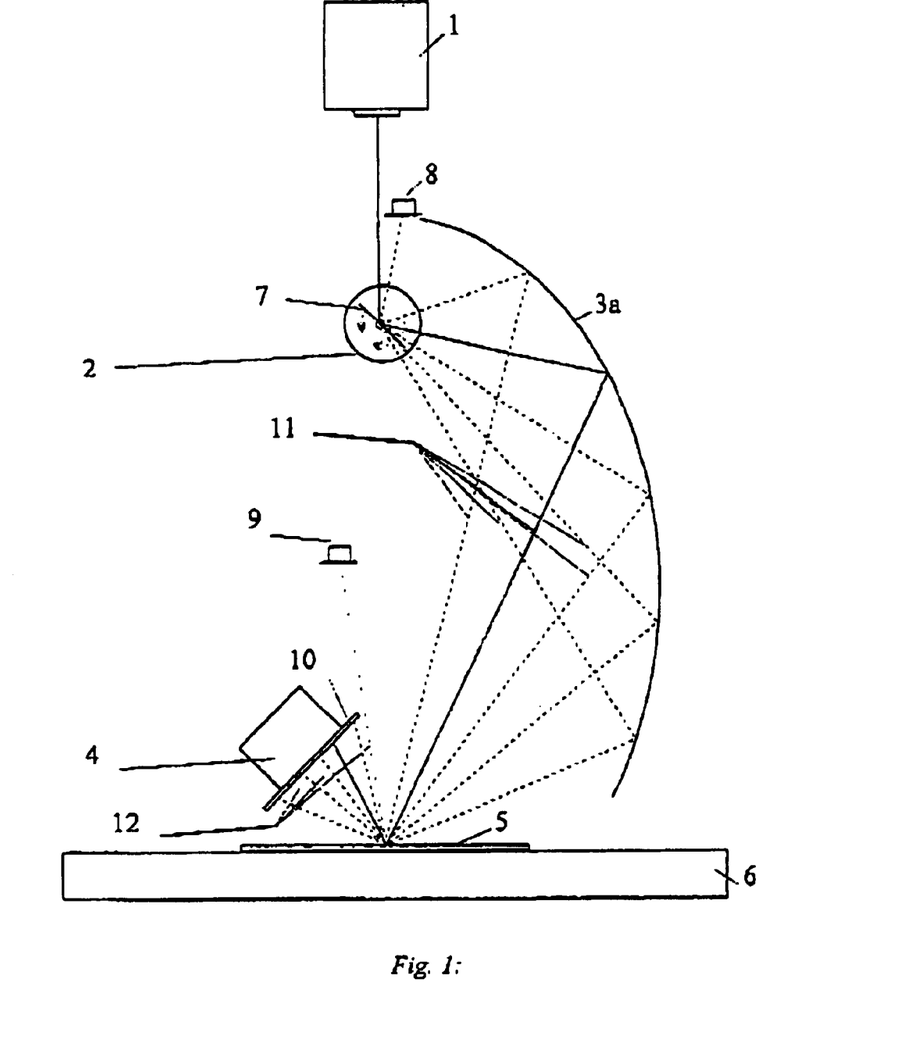
FIG. 1 is a sectional view showing a device varying the perpendicular angle of incidence.

Referring now to the figures of the drawings in detail and first, particularly to FIG. 1 thereof, there is shown a device, which can be used to vary the perpendicular angle φ of incidence (in the plane of incidence or the plane of the drawing). A light source 1, e.g. a laser, generates coherent light. The measuring beam is directed to a measuring configuration via fiber-optics configurations or directly. At the measuring configuration, the measuring beam impinges—possibly with the aid of a deflection mirror—on a device for deflection 2 in different directions, e.g. a rotatable mirror surface 7. The axis of rotation of the mirror surface 7 is perpendicular to the plane of incidence of the measuring beam. The mirror is rotated electrically in a manner regulated to an accuracy of a few μrad, preferably with the aid of a so-called galvanometer scanner. From the scanner mirror, the deflected measuring beam impinges on an ellipsoidal mirror 3a. If the point of intersection between the measuring beam and the scanner mirror is situated at the focal point of the ellipsoidal mirror, then a special property of the ellipsoidal mirror is manifested: it has two focal points. The light beams for different galvanometer angles therefore meet at one point. If the location of the specimen is chosen such that the measurement point corresponds to the second focal point, then the fixed measurement point is irradiated with variable angles of incidence by rotation of the scanner mirror. Since the scanner reaches specific angular positions within a few milliseconds, the measuring beam 11 can very rapidly traverse a large angular range and realize the measuring beam parameter variation that is required for a diffraction analysis. The ellipsoidal form of the mirror may be composed of individual segments and the ellipsoidal mirror may be shaped as a rotational body, so that even in the event of azimuthal angle deviations (e.g. rotation of the scanner about the axis of the incident measuring beam), the measuring beams are focused at the measurement point. The mirror surface of the galvanometer scanner must be located in the center point of the axis of rotation in order that the reflection point is always situated at the focal point of the ellipsoidal mirror. If this precondition is not provided, then the measuring beam, during the change in the angle of incidence, sweeps over a certain region of the specimen surface around the central measurement point. This may be desirable for specific applications, in order to increase the measurement region without altering the diameter of the measuring beam.

The coherent measuring beam is diffracted at the periodic structures of the specimen 5. If the grating vector—which identifies the direction of the periodicity of the grating structures—lies in the plane of incidence, then higher orders of diffraction that may occur are likewise situated in the plane of incidence. If this precondition is not met, then so-called "conical diffraction" occurs and all the diffraction maxima apart from the direct reflection lie on an arc perpendicular to the plane of incidence, i.e. the diffraction maxima no longer lie in the plane of the drawing. In the case of non-conical diffraction, the intensities of the diffracted radiation 12 can be measured by a detector unit 4 containing a photodiode linear array 10, which is inclined above the specimen in the plane of the drawing. If the number of individual diodes is large enough, then the individual intensities of all the diffraction maxima that can be detected can be measured. Since an intensity value measured by photodiodes depends on the angle of incidence of a light beam on the diode surface, the diode array must be appropriately calibrated. As an alternative, it is possible to configure a plurality of individual diodes on a semicircle around the measurement point. The orders of diffraction then always impinge perpendicularly on the photodiodes. A further possibility includes using a single large-area photodiode. The measured value obtained in this case is the summation intensity of the diffracted light beams, which can likewise be used for calculating or classifying the structural parameters on the specimen.

In order to increase the accuracy of the measuring configuration, the noise of the light source can be compensated by repeated reference measurements. To that end, either the beam emerging from the light source is split (e.g. by an optical beam splitter) and the intensity of a beam is measured by a photometer or a photodiode. Optionally, this radiation detector 8 also can be configured in such a way that the measuring beam impinges on it at a specific angular position of the galvanometer (possibly also via a deflection mirror). Preceding beam splitting is then obviated.

The measurement method reacts very sensitively to changes in the angle of incidence, as occur e.g. through tilting or undulation of the substrate to be examined. With the aid of a PSD (position sensitive device) 9, on which the direct reflection impinges at a specific angle of incidence, such tilting can be detected and taken into account during the evaluation of measurement data. As an alternative, the angular error can also be corrected by a piezo element, which determines the position of the specimen. With the aid of an xy measurement table 6, it is possible to move to different measurement points on the specimen. optionally, the specimen can also be fixed and the mirror and detector unit is moved accordingly.

Figure 2:
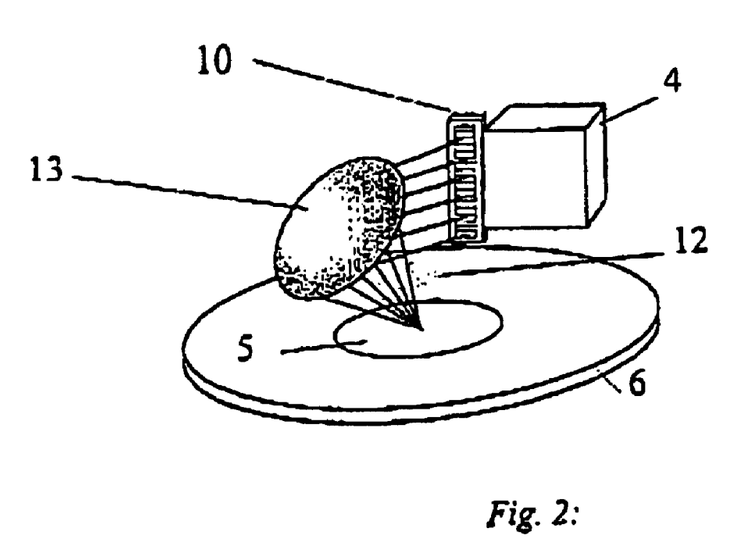
FIG. 2 is a perspective view showing a device measuring intensity indirectly with a mirror.

FIG. 2 shows how it is furthermore possible to realize an indirect intensity measurement using one or more mirrors 13. What are appropriate for this are e.g. planar deflection mirrors, which, under certain circumstances, simplify the construction of the measuring configuration, and also spherical and aspherical mirrors that can be used to focus the orders of diffraction. The angular range that can be detected can thus be increased and/or the required dimensions of the photodiode linear array 10 can be reduced. For the case of conical diffraction, rectangular or square photodiode arrays or CCDs can be used for the measurement of diffraction maxima. In order to detect a large solid angle range, a mirror for focusing the diffraction pattern onto the detector array is usually used for this purpose. The mirror for deflecting the diffraction effects can, moreover, also include individual segments.

Figure 3:
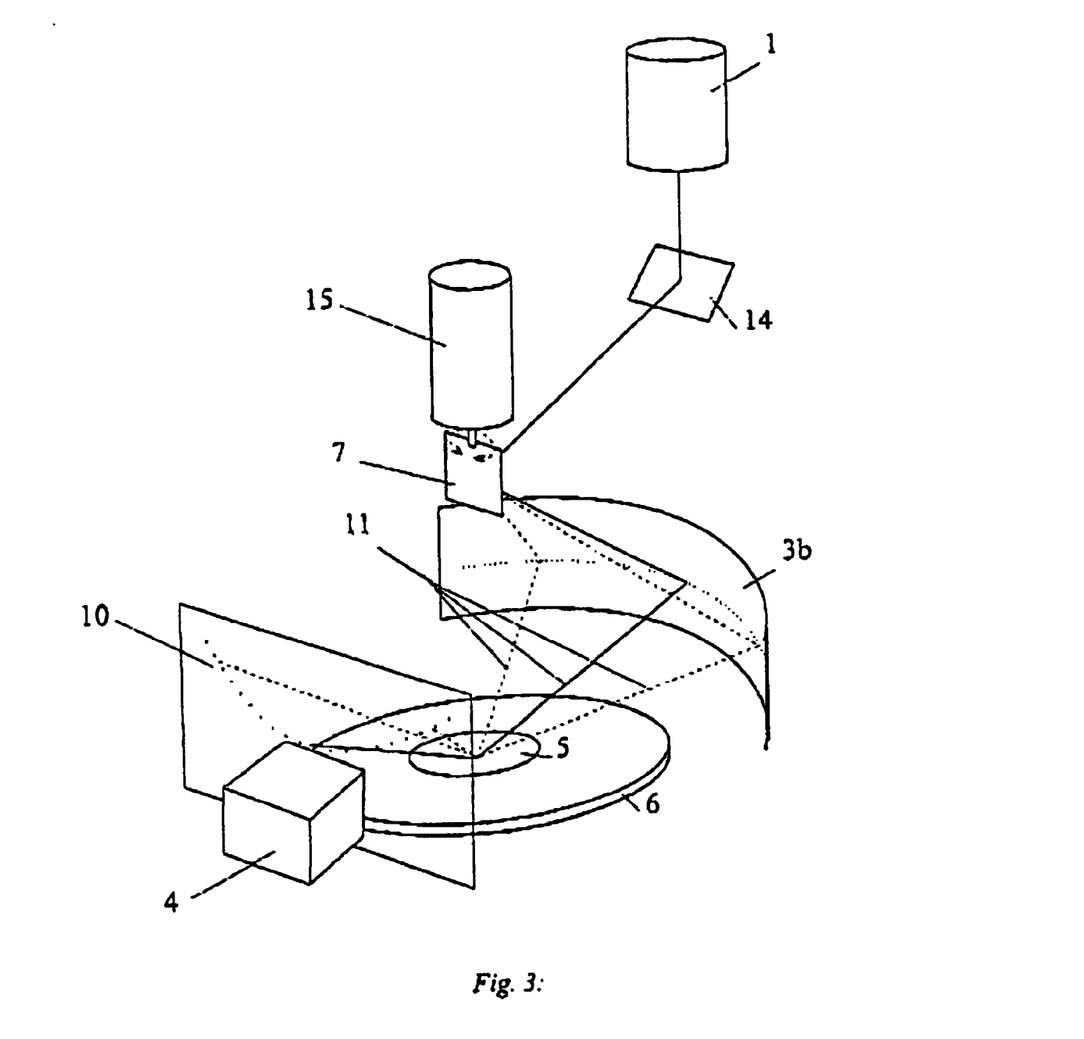
FIG. 3 is a perspective view showing a device varying the azimuth of the measuring beam varies relative to the specimen surface.

In FIG. 3, the azimuth of the measuring beam is varied relative to the specimen surface. The intensity profiles of the diffraction maxima as a function of the azimuthal angle once again serve for characterizing the specimen surface. As in the configuration described above, use is made of a coherent light source 1, possibly in conjunction with a fiber-optics configuration and/or deflection mirrors 14. The measuring beam is once again reflected in different directions with the aid of a galvanometer scanner 15. If the configuration of the components is chosen in accordance with FIG. 3 and if the point of intersection between measuring beam and scanner mirror is situated at the radius center point or focal point of a concentric mirror 3b (or mirror segment), then the deflected measuring beams 11 again impinge under different angles on one point which is chosen as the measurement point.

Since the position of the plane of incidence changes in this case, conical diffraction always occurs with periodically patterned substrates (specimen 5). The zero-order direct reflection runs on a chrome surface whose vertex forms the measurement point. If a planar array of photodiodes 10 is used for the intensity measurement of the zero-order diffraction, the individual diodes must therefore be situated along a correspondingly curved line. As an alternative, a rectangular diode array or a CCD could also be used in order to form a spatially resolved intensity measurement. As a result, higher orders of diffraction can also be measured and assigned. As described for the case of the first measuring configuration, it is again possible, furthermore, to use planar, spherical or aspherical mirrors for deflecting or focusing the diffraction effects.

Figure 4:
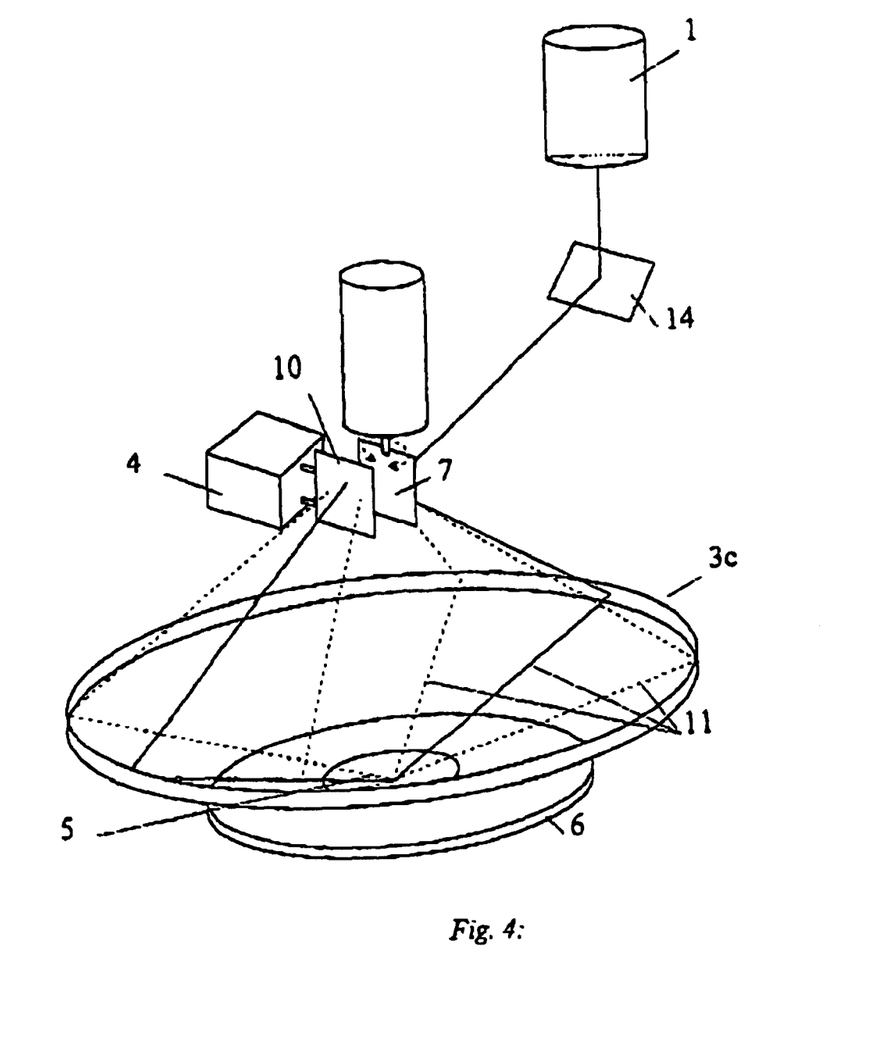
FIG. 4 is a perspective view showing a measuring device.

FIG. 4 illustrates a further variant of the measuring device. The reflection mirror used is the same mirror or a similar mirror with a different radius, as for the deflection of the measuring beams onto the specimen. As a special case, the two mirrors may be combined and form an inwardly mirrored ring (3c. Depending on the embodiment, the zero-order diffractions reflected by the specimen 5 are focused in the vicinity of the scanner mirror. If a large-area photodiode 10 is introduced in front of that, then it is possible to measure the intensity of the zero-order diffraction, the diode having to be calibrated for different angles of incidence. The height of the mirror ring 3c should be chosen to be as small as possible in this embodiment. Because higher orders of diffraction occur under different solid angles, what can thus be achieved is that generally only the intensity of the zero-order diffraction is measured. In the case of specific structural forms, only a cumulative measurement of a plurality of orders of diffraction is possible, under certain circumstances. However, this also leads to measurement results, which allow the specimen to be characterized.

With regard to reference measurements of the intensity of the light source, the use of PSD elements and the moving of measurement table or measurement setup, the statements made for the first measurement setup are applicable.

A further embodiment of the measuring configurations described uses a micro-optical module for beam deflection, as proposed e.g. in EP 0712505 B1, which corresponds to U.S. Pat. No. 5,920,662. The mechanically moved scanner component can thus be replaced. The change in the angle of the measuring beam is in this case achieved by utilizing electro-optical properties of suitable materials. The sequential production of different angles of incidence with the aid of a spherical or aspherical mirror or with the aid of mirror segments remains characteristic of the measuring configuration.

The measuring configuration is simplified further by using the rear side of the scanner mirror. To that end, the beams reflected from the substrate are focused with the aid of the same mirror form that is responsible for focusing downstream of the beam deflection with the scanner in the first step. If the photodiode is removed (e.g. in FIG. 4) then the reflected beams meet at one point on the rear side of the scanner mirror. From this point, the beams always run in the same direction in an extension of the beam incident on the scanner mirror. A photodiode can then be introduced into the reflected beam, the angle of incidence of the measuring beam on the photodiode remaining constant irrespective of the position of the scanner mirror. The same principle is also possible for the variation of the angle of incidence in the plane of incidence in FIG. 1. On the side opposite to the first mirror, an identical ellipsoidal mirror realizes the focusing of the reflected beams onto the rear side of the scanner mirror. From there, the beams run in an extension of the measuring beam incident from the light source. In this case, too, the intensities can be measured using a single photodiode: the angle of incidence on the photodiode remaining practically constant.

In a method for measuring angle-dependent diffraction effects, first, a coherent beam is generated. This beam experiences a first deflection in a temporally successively sequential manner in different directions. The coherent beam is then deflected a second time onto a specimen. A diffracted beam is produced through diffraction of the coherent beam at the specimen. This diffracted beam is detected. The apparatus described above can be operated using this method.

Preferably, a signal corresponding to the direction of the first deflection and a signal corresponding to the detected diffracted beam are generated and these two signals are assigned to one another. This enables angle-dependent diffraction signal detection. An angle-dependent diffraction signal thus obtained is characteristic of a specimen class and makes it possible to classify an unknown specimen.

We claim:

1. An apparatus for measuring angle-dependent diffraction effects, comprising:
   a coherent radiation source producing coherent radiation;
   a device for deflecting rays of the coherent radiation in different directions;
   a concentric mirror having an axis of symmetry and a centerpoint, said concentric mirror reflecting the rays arriving differently and sequentially one after the other from said device for deflecting the coherent radiation to a focal point;
   a detector unit for measuring the intensity of the radiation diffracted by a specimen having a measuring point located at the focal point;
   said device for deflecting the coherent beam being situated on said axis of symmetry of said concentric mirror; and
   the measuring point on the specimen being disposed on said axis of symmetry of said concentric mirror symmetrically and equidistantly from said center point of said concentric mirror as said device for deflecting the coherent beam.

2. The apparatus according to claim 1, wherein said concentric mirror is formed of mirror segments disposed to act as a single concentric mirror.

3. The apparatus according to claim 1, wherein said device for deflecting the coherent radiation includes an electrically regulated rotating mirror.

4. The apparatus according to claim 3, wherein:
   said concentric mirror has an axis of symmetry;
   said device for deflecting the coherent beam is situated on said axis of symmetry of said concentric mirror; and
   said rotating mirror has an axis of rotation coinciding with said axis of symmetry and is always impinged by the coherent beam at a point on said axis of symmetry.

5. The apparatus according to claim 1, wherein said device for deflecting the coherent radiation includes a micro-optical module.

6. The apparatus according to claim 5, including a mirror reflecting the radiation diffracted at the specimen onto the detector.

7. The apparatus according to claim 6, wherein said mirror for directing the diffracted radiation indirectly onto said detector unit resembles said concentric mirror.

8. The apparatus according to claim 7, wherein said mirror and said concentric mirror form a mirrored ring.

9. The apparatus according to claim 1, wherein said device for deflecting the coherent radiation includes an electro-optical module.

10. The apparatus according to claim 9, including a mirror reflecting the radiation diffracted at the specimen onto the detector.

11. The apparatus according to claim 10, wherein said mirror for directing the diffracted radiation indirectly onto said detector unit resembles said concentric mirror.

12. The apparatus according to claim 11, wherein said mirror and said concentric mirror form a mirrored ring.

13. The apparatus according to claim 1, wherein said detector unit includes a photodiode linear array.

14. The apparatus according to claim 1, wherein said detector unit includes a plurality of individual diodes.

15. The apparatus according to claim 1, wherein said detector unit includes a single large-area photodiode.

16. The apparatus according to claim 1, wherein said detector unit includes photodiode arrays.

17. The apparatus according to claim 1, wherein said detector unit includes CCDs.

18. The apparatus according to claim 1, including a radiation detector being impinged upon by a beam when said deflection device is specifically positioned.

19. The apparatus according to claim 1, including:
a beam splitter splitting the beam to create partial beams; and
a radiation detector being impinged upon by a partial beam from said beam splitter when said deflection device is specifically positioned.

20. The apparatus according to claim 1, including:
a position sensitive device detecting a change in the angle of incidence through tilting and surface undulations of the specimen; and
a piezoelement correcting for the change in the angle of incidence through tilting and the surface undulations of the specimen when measured data is evaluated.

21. The apparatus according to claim 1, including:
a CCD detecting a change in the angle of incidence through tilting and surface undulations of the specimen; and
a piezoelement correcting for the change in the angle of incidence through tilting and the surface undulations of the specimen when measured data is evaluated.

22. The apparatus according to claim 1, including an xy measurement table positioning the specimen to measuring different measurement points on a specimen.

23. An apparatus for measuring angle-dependent diffraction effects, comprising:
a coherent radiation source producing coherent radiation;
a device for deflecting rays of the coherent radiation in different directions, said device for deflecting the coherent radiation including an electrically regulated rotating mirror;
a concentric mirror having an axis of symmetry and a center point, said concentric mirror reflecting the rays arriving differently and sequentially one after the other from said device for deflecting the coherent radiation to a focal point; and
a detector unit for measuring the intensity of the radiation diffracted by a specimen having a measuring point located at the focal point, wherein:
said device for deflecting the coherent beam is situated on said axis of symmetry of said concentric mirror;
said rotating mirror has an axis of rotation coinciding with said axis of symmetry and said rotating mirror is always impinged by the coherent beam at a point on said axis of symmetry; and
the measurement point on the specimen is disposed on said axis of symmetry of the concentric mirror symmetrically and equidistantly from said center point of said concentric mirror as said device for deflecting the coherent beam.

24. The apparatus according to claim 23 including a mirror reflecting the radiation diffracted at the specimen onto the detector.

25. The apparatus according to claim 24, wherein said concentric mirror is said mirror for directing the diffracted radiation indirectly onto said detector unit resembles said concentric mirror.

26. The apparatus according to claim 25, wherein said mirror and said concentric mirror form a mirrored ring.

27. The apparatus according to claim 25, wherein said electrically regulated rotating mirror is for further deflecting the diffracted radiation onto said detector element.

28. An assembly for measuring angle-dependent diffraction effects, comprising:
an apparatus having a coherent radiation source producing coherent radiation, a device for deflecting rays of the coherent radiation in different directions, a concentric mirror having an axis of symmetry and a center point, said concentric mirror reflecting the rays from the device for deflecting the coherent radiation differently and sequentially one after the other at a focal point, a detector unit for measuring the intensity of the radiation diffracted by a specimen having a measuring point located at the focal point, said device for deflecting the coherent beam being situated on said axis of symmetry of said concentric mirror, the measuring point on the specimen being disposed on said axis of symmetry of said concentric mirror symmetrically and equidistantly from said center point of said concentric mirror as said device for deflecting the coherent beam; and
a positioner for positioning the apparatus relative to the specimen.

* * * * *

UNITED STATES PATENT AND TRADEMARK OFFICE
CERTIFICATE OF CORRECTION

PATENT NO. : 6,724,475 B2  Page 1 of 1
DATED : April 20, 2004
INVENTOR(S) : Norbert Benesch et al.

It is certified that error appears in the above-identified patent and that said Letters Patent is hereby corrected as shown below:

<u>Title page,</u>
Item [73], Assignee, should read -- Semiconductor300 GmbH & Co. KG, Dresden (DE) Fraunhofer-Gesellschaft zur Förderung der angewandten Forschung e.V., München (DE) --.

Signed and Sealed this

Twenty-fifth Day of April, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,724,475 B2 | Page 1 of 1 |
| APPLICATION NO. | : 09/968587 | |
| DATED | : April 20, 2004 | |
| INVENTOR(S) | : Norbert Benesch et al. | |

It is certified that error appears in the above-identified patent and that said Letters Patent is hereby corrected as shown below:

<u>Title page,</u>
Item [73], Assignee, should read -- Semiconductor300 GmbH & Co. KG, Dresden (DE) Fraunhofer-Gesellschaft zur Förderung der angewandten Forschung e.V., München (DE) --.

This certificate supersedes Certificate of Correction issued April 25, 2006.

Signed and Sealed this

Twentieth Day of June, 2006

JON W. DUDAS
*Director of the United States Patent and Trademark Office*